United States Patent [19]

Panzera et al.

[11] Patent Number: 5,614,330

[45] Date of Patent: Mar. 25, 1997

[54] PORCELAIN COATING COMPOSITIONS FOR LOW EXPANSION PORCELAIN CORES AND THE RESULTING ALL-CERAMIC DENTAL RESTORATIONS

[75] Inventors: Carlino Panzera; Jana N. Pruden, both of Belle Mead; Richard A. Brightly, Westwood, all of N.J.

[73] Assignee: American Thermocraft Corporation, Somerset, N.J.

[21] Appl. No.: 516,579

[22] Filed: Aug. 18, 1995

[51] Int. Cl.$^6$ .................................................. B32B 9/00
[52] U.S. Cl. ............................ 428/697; 428/70; 428/76; 428/404; 428/699; 428/701; 428/702; 106/35; 433/206; 433/212.1; 501/14; 501/21; 501/25; 501/27
[58] Field of Search .................... 433/206, 212.1; 106/35; 501/14, 21, 25, 57; 428/699, 701, 702, 697, 70.76, 404

[56] References Cited

U.S. PATENT DOCUMENTS

| | | | |
|---|---|---|---|
| 2,414,633 | 1/1944 | Bryant | 501/25 |
| 3,008,841 | 11/1961 | Tiede | 501/35 |
| 3,098,753 | 7/1963 | Van Dolah | 501/25 |
| 3,765,931 | 10/1973 | Kyri | 501/25 |
| 3,836,373 | 9/1974 | Ault | 501/25 |
| 4,120,729 | 10/1978 | Smyth | 501/25 |
| 4,386,162 | 5/1983 | Beall | 501/3 |
| 4,386,164 | 5/1983 | Moser | 501/66 |
| 4,431,451 | 2/1984 | Mabie et al. | 106/35 |
| 4,437,192 | 3/1984 | Fujiu | 501/25 |
| 4,467,039 | 8/1984 | Beall et al. | 501/3 |
| 4,551,099 | 11/1985 | Panzera | 433/212.1 |
| 4,775,592 | 10/1988 | Akahane et al. | 428/406 |
| 4,789,649 | 12/1988 | Abert et al. | 501/3 |
| 4,828,117 | 5/1989 | Panzera | 206/63.5 |
| 5,009,709 | 4/1991 | Ibsen et al. | 106/35 |
| 5,281,563 | 1/1994 | Komma et al. | 501/59 |
| 5,346,866 | 9/1994 | Komma | 501/25 |
| 5,382,552 | 1/1995 | Saad et al. | 501/25 |

*Primary Examiner*—Ellis Robinson
*Assistant Examiner*—Timothy M. Speer
*Attorney, Agent, or Firm*—Cummings & Lockwood

[57] ABSTRACT

An all-ceramic dental restoration comprising a ceramic core over and at least one coating thereon of a porcelain composition having a maturing temperature of from about 850° to about 1050° C. and a coefficient of thermal expansion of from about 4.0 to about 13 (room temperature to 500° C.) parts per million per °C. comprising:

| Component | Amount (Wt. %) |
|---|---|
| $SiO_2$ | 69–75 |
| $Al_2O_3$ | 4.0–9.5 |
| $Na_2O$ | 5–10 |
| $K_2O$ | 0–4 |
| $CaO$ | 0–1.5 |
| $MgO$ | 0–6 |
| $B_2O_3$ | 6–15 |
| F | 0–3 |

13 Claims, No Drawings

PORCELAIN COATING COMPOSITIONS FOR LOW EXPANSION PORCELAIN CORES AND THE RESULTING ALL-CERAMIC DENTAL RESTORATIONS

This invention relates to dental porcelain compositions having thermal expansion values lower than the values typically associated with commercially available porcelain used for porcelain-fused-to-metal applications. The porcelains of the present invention are especially suitable for application to all-ceramic copings.

BACKGROUND OF THE INVENTION

Dental restorations such as dental crowns and bridges are generally made using a metallic framework coated with a fused dental porcelain to provide the desired aesthetics. Today, however, there is an increasing tendency to use non-metallic materials for this purpose, particularly high strength porcelains which provide a more natural translucency and therefore, much improved aesthetics. These porcelain materials exhibit coefficients of thermal expansion much lower than the dental alloys used in porcelain-fused-to-metal applications, e.g., $5-8\times10^{-6}$ as compared to $13-14\times10^{-6}$ (room temperature to 500° C.) parts per million (ppm) per °C.

Accordingly, it is the object of the present invention to provide dental porcelain compositions which mature at a temperature consistent with the thermal stability temperature of ceramic cores and are chemically and thermally stable.

It is another object of the present invention to provide porcelain compositions which form a chemical bond with all-ceramic cores and which have a thermal expansion value of about 1 to 1.5 ppm per °C. less than the expansion of the core which places the porcelain in slight compression when the fused restoration cools to room temperature.

It is yet another object to provide improved all-ceramic dental restorations.

SUMMARY OF THE INVENTION

These as well as other objects and advantages are provided by the present invention which comprises a porcelain composition having a maturing temperature which ranges from about 850° to about 1050° C. and a coefficient of thermal expansion of from about 4.0 to 13 (room temperature to 500° C.) parts per million per °C. and comprises:

| Component | Amount (Wt. %) |
| --- | --- |
| $SiO_2$ | 69–75 |
| $Al_2O_3$ | 4.0–9.5 |
| $Na_2O$ | 5–10 |
| $K_2O$ | 0–4 |
| CaO | 0–1.5 |
| MgO | 0–6 |
| $B_2O_3$ | 6–15 |
| F | 0–3 |

DETAILED DESCRIPTION OF THE INVENTION

Several low expansion ceramic cores which have thermal expansion values lower than conventional porcelain fused to metal porcelains are currently on the market. Some of these core materials are aluminum based, e.g., In-Ceram, Hi-Ceram and Vitadur N manufactured by Vita Zahnfabrik of Bad Sackingen, Germany. Some core materials are castable and machinable such as Dicor glass-ceramic (mica glass) manufactured by Corning Glass Co. of Corning, N.Y. These core materials have a thermal expansion value, from room temperature to 500° C. of about 7–8 parts per million per °C. The In-Ceram and Dicor materials are dimensionally stable at 950° C. and lower; the others are typically fabricated on an inert refractory die as is well known in the art.

The dental porcelain compositions of the present invention comprise:

| Component | Range (wt %) | Preferred (wt %) | Most Preferred (wt %) |
| --- | --- | --- | --- |
| $SiO_2$ | 69–75 | 71–74 | 73.1 |
| $Al_2O_3$ | 4.0–9.5 | 6.0–8.0 | 6.85 |
| $Na_2O$ | 5–10 | 6.0–8.0 | 6.85 |
| $K_2O$ | 0–4 | 2–4 | 3.6 |
| CaO | 0–1.5 | 0.8–1.5 | 1.3 |
| MgO | 0–6 | 0–2.0 | 0.8 |
| $B_2O_3$ | 6–15 | 7.0–10.0 | 7.5 |
| F | 0–3 | 0–2.0 | 0.0 |
| Thermal Expansion (RT to 500° C.) parts per million per °C. | 4.0–13 | 5.5–8.5 | 5.8–6.2 |
| Maturing Temp. | | | |
| °C. | 850–1050 | 900–1000 | 925 |
| °F. | 1562–1922 | 1652–1832 | 1700 |

The dental porcelains of the present invention are amorphous glasses which mature at a temperature consistent with the thermal stability temperature of ceramic cores and are chemically and thermally stable. That is, the porcelain forms a chemical bond with the core and has a thermal expansion value of about 1 to 1.5 ppm per °C. less than that of the core which places the porcelain in slight compression when the fused restoration cools to room temperature.

The fused porcelain has sufficient viscosity at the maturing temperature such that it does not lose its shape, yet fires to nearly 100% of theoretical density, thus forming a tight impervious surface necessary in the oral environment. Moreover, the viscosity of the porcelain is such that the composition is readily castable. The porcelain composition of the present invention is also machinable thereby lending itself to CAD/CAM fabrication techniques.

The porcelain compositions of this invention can be prepared by melting together sufficient precursor components to yield the compositions shown in the above table. Suitable precursors include silica, alumina, boric acid, feldspar, calcium carbonate, sodium carbonate, potassium carbonate, or if desired, the actual oxides, blended in proportion to yield the compositions shown in the above table.

The preparation of such materials is well known in the art. After the materials are blended, preferably in finely divided powder form such as powder sufficiently fine to pass through a 200 mesh screen (Tyler series), the precursors and/or oxides are heated to a temperature of at least about 1200° C., and preferably to at least about 1500° C., in a crucible to form a glass. The molten glass may then be quenched in water, dried, and ground in a ball mill, to provide the porcelain material of the present invention in the form of a powder. It is preferred that the powder is ground finely enough so that it will pass through a 160 mesh screen (Tyler series).

The properties of the porcelain composition can be adjusted by applying the following well known principles:

Within the ranges of component proportions set forth in the above table, the coefficient of thermal expansion can be increased, if desired, by decreasing the proportion of $SiO_2$ and/or $B_2O_3$ and/or by increasing the proportion of the alkali metal oxides. The fusion point can be reduced by increasing the proportion of $B_2O_3$, CaO, and/or the alkali metal oxides. As between the two alkali metal oxides, an increase in the $Na_2O:K_2O$ ratio lowers the fusion point. It is well within the skill of the ceramics art to apply these principles to make fine adjustments to the thermal expansion coefficients and fusion temperatures.

If desired, in order to assure proper aesthetics, one or more layers of the porcelain composition of the present invention can be applied over the core with each layer being separately fired. Thus, for example, an opaceous layer containing an opacifying agent such as $TiO_2$, $SnO_2$, $Al_2O_3$, ZnO, $CeO_2$, and the like can be applied over the core and fired. Thereafter, or in lieu thereof, a stain layer can be applied containing one or more conventional pigments such as vanadates, manganates, chromates, or other transition metal compounds, to tint the stain layer to the desired shade. The opaceous and/or stain layer can then be overcoated (after sequential firing) with a translucent layer of the porcelain composition of the present invention. In this manner, special effects can be obtained, e.g., a different shade at the tip of the restoration than at the gingival area. The layers are applied to the core in the usual manner, as by applying a paste of the porcelain powder in water over the core, shaping to the desired configuration, and then firing.

Further variations and modifications of the present invention will become apparent to those skilled in the art from the foregoing and are intended to be encompassed by the claims appended hereto.

What is claimed is:

1. An all-ceramic dental restoration comprising a ceramic core and at least one coating thereon of a porcelain composition having a maturing temperature of from about 850° to about 1050° C. and a coefficient of thermal expansion of from about 4.0 to about 13 parts per million per °C. from room temperature to 500° C., said porcelain composition comprising:

| Component | Amount (Wt. %) |
|---|---|
| $SiO_2$ | 69–75 |
| $Al_2O_3$ | 4.0–9.5 |
| $Na_2O$ | 5–10 |
| $K_2O$ | 0–4 |
| CaO | 0–1.5 |
| MgO | 0–6 |
| $B_2O_3$ | 6–15 |
| F | 0–3. |

2. An all-ceramic dental restoration as defined in claim 1 where at least one opaceous porcelain layer is interposed between the core and the porcelain coating.

3. An all-ceramic dental restoration is defined in claim 2 wherein the porcelain coating is translucent.

4. An all-ceramic dental restoration as defined in claim 1 where at least one tinted porcelain layer is interposed between the core and the porcelain coating.

5. An all-ceramic dental restoration comprising a ceramic core and at least one coating thereon of a porcelain composition having a maturing temperature of from about 900° to 1000° C. and a coefficient of thermal expansion of from about 5.5 to about 8.5 parts per million per °C. from room temperature to 500° C., said porcelain composition comprising:

| Component | Amount (Wt. %) |
|---|---|
| $SiO_2$ | 71–74 |
| $Al_2O_3$ | 6.0–8.0 |
| $Na_2O$ | 6.0–8.0 |
| $K_2O$ | 2–4 |
| CaO | 0.8–1.5 |
| MgO | 0–2.0 |
| $B_2O_3$ | 7.0–10.0 |
| F | 0–2.0. |

6. An all-ceramic dental restoration as defined in claim 5 where at least one opaceous porcelain layer is interposed between the core and the porcelain coating.

7. An all-ceramic dental restoration as defined in claim 6 wherein the porcelain coating is translucent.

8. An all-ceramic dental restoration as defined in claim 5 where at least one tinted porcelain layer is interposed between the core and the porcelain coating.

9. A porcelain composition having a maturing temperature of about 925° C. and a coefficient of thermal expansion of from about 5.8 to about 6.2 parts per million per °C. from room temperature to 500° C., comprising:

| Component | Amount (Wt. %) |
|---|---|
| $SiO_2$ | 73.1 |
| $Al_2O_3$ | 6.85 |
| $Na_2O$ | 6.85 |
| $K_2O$ | 3.6 |
| CaO | 1.3 |
| MgO | 0.8 |
| $B_2O_3$ | 7.5 |

10. Am all-ceramic dental restoration comprising a ceramic core and at least one coating thereon of the porcelain composition as defined in claim 9.

11. An all-ceramic dental restoration as defined in claim 10 where at least one opaceous porcelain layer is interposed between the core and the porcelain coating.

12. An all-ceramic dental restoration as defined in claim 11 wherein the porcelain coating is translucent.

13. An all-ceramic dental restoration as defined in claim 10 where at least one tinted porcelain layer is interposed between the core and the porcelain coating.

* * * * *